Aug. 22, 1972 M. B. WAKEFIELD Plant Pat. 3,261
DOGWOOD TREE
Filed March 5, 1971
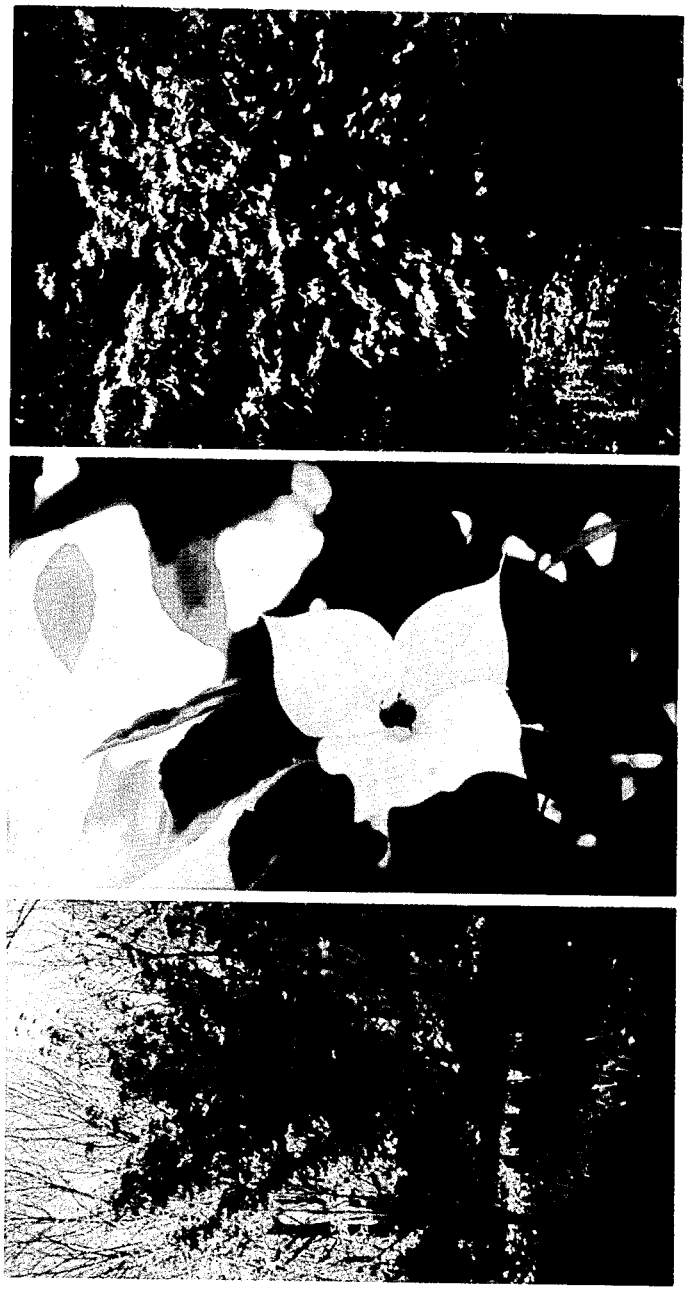
Inventor.
Mary B. Wakefield.
By: Robb & Robb
Attorneys.

United States Patent Office

Plant Pat. 3,261
Patented Aug. 22, 1972

3,261
DOGWOOD TREE

Mary B. Wakefield, 1465 Brush Hill Road,
Milton, Mass. 02186

Filed Mar. 5, 1971, Ser. No. 121,607
Int. Cl. A01h 5/00
U.S. Cl. Plt.—51 1 Claim The present invention relates to a new and distinct variety of dogwood tree of the Japanese dogwood type botanically known as *Cornus kousa*, which was originated by me from a seed which was initially processed and then planted by me indoors in my house, and then set out as a young seedling plant in my nursery located at Milton, Mass.

When I acquired this seed, I was attending classes on plant propagation, as conducted at the Arnold Arboretum which is near my home in Milton, Mass. My interest in plant propagation and experimentation led me to seek and receive permission to obtain seeds of various plants, including dogwoods, being grown at the Arnold Arboretum. This particular seed was taken by me from the largest-fruited dogwood tree specimen of the *kousa* type which had attracted my attention at the Arboretum, but which was of uncertain origin and parentage. In a few years, I observed that my new seedling had an unusual vase-shape and the flowers were unusually wide-bracted and somewhat cupped, without ever becoming flat, and the flowers bloom about ten days later and longer than most other dogwood varieties being grown by or otherwise known to me. Accordingly, and in due course, I arranged to have my new seedling propagated on my behalf by rooted cuttings, and I have kept the original seedling and its progeny under close observation.

As the result of my observations and tests as aforementioned, I am convinced that my new seedling is a new and improved dogwood variety which is distinguished from its parent, as well as from all other varieties of which I am aware, and that its unusual characteristics originally observed, among others later observed, come true and are established and transmitted through succeeding propagations. These characteristics and distinctions represent a unique and commercially valuable combination of features, as evidenced by the following which are outstanding therein:

(1) A sturdy, graceful, upright arching, vase-shaped habit of growth;
(2) Smooth exfoliating bark;
(3) Attractive yellowish-green leaves which turn bright deep red in autumn and are retained on the tree as one of the last of the deciduous trees to drop its leaves;
(4) Large, showy, neat flowers, which are composed of broadly based overlapping bracts which curve to pointed tips and remain slightly cupped and present a crisp sculptured appearance throughout the flowering season which begins early in the month of June and extends well into July in Massachusetts;
(5) A distinctive and attractive flower color which is a creamy white color when the flowers first appear and then turning pure white in a few days, but sometimes having a pale pink tinge when opening and again when ready to drop;
(6) Large attractive and long-lasting fruit whch gradually turn in color from yellow-green, to yellow, to orange and then to bright red until the fruit drops, with some fruit in the various color stages being on the tree at the same time throughout most of the season;
(7) Excellent hardiness to at least −20° F. without injury; and
(8) Especial suitability for planting in patios, lawns, alleys, and to flank features of special interest.

The accompanying drawing shows a typical young tree specimen in bloom and also after the foliage changes to its red color in autumn, as well as a typical individual flower specimen on a larger scale, as depicted in color as nearly true as it is reasonably possible to make the same in a color illustration of this character.

The following is a detailed description of my new dogwood variety, with color terminology in accordance with the Royal Horticultural Colour Chart, published by the Royal Horticultural Society of London, except where general color terms of ordinary dictionary significance are obvious:

Breeding: A seedling of an unnamed and unpatented variety of the species *C. kousa* of uncertain origin and parentage.
Propagation: Holds its distinguishing characteristics through succeeding propagations by rooted cuttings.
Locality where grown and observed: Milton, Mass.
Tree: Small; upright; from about 15 feet to 20 feet tall; hardy to at least −20° F.
*Trunk.*—Slender; with smooth exfoliating bark.
*Branches.*—Firm; rather slender; arching. Color (bark)—Grey-brown, from Plate 199A to 201B.
Foliage:
*Leaves.*—Length—from about 3¾ inches to 4¼ inches. Width—from about 2 inches to 2⅜ inches. Shape—elliptic ovate, with caudate tip; with tufts of rich brown hairs in the axle of the upper surface and two pairs of veins on the lower surface of the leaf. Color—Yellow-Green, Plate 144A, changing in Autumn to Grey-Red, Plate 181C. Margin—obscurely crenate. Petiole—from about ¼ inch to ⅜ inch long.
Flower buds:
*Hardiness.*—Hardy to at least −20° F.
*Size.*—Length—about 5/16 inch. Width—about ¼ inch.
*Shape.*—Broadly fusiform.
*Color.*—Grey-Brown, Plate 200C.
Flowers (Inflorescence):
*Dates of first and full bloom.*—About June 6 and June 16, respectively, at Milton, Mass.
*Quantity.*—Abundant.
*Size.*—Large (up to about 5 inches in diameter).
*Petalage (bracts).*—Number of bracts—4. Shape—from elliptic to ovate, with caudate tips. Size—Length—from about 2⅛ inches to 2 5/16 inches. Width—from about 1⅝ inches to 1 13/16 inches. Color—pure white when mature, but usually creamy when first appearing and then turning white in few days, and sometimes having a pink tinge when opening and again when ready to drop.
Fruit:
*Size.*—About 1 inch in diameter.
*Color.*—Yellow-Green, Plate 144A, then changing through Yellow, Plate 10, then through Orange, Plate 29B to Red, Plate 45A.
General observations: My new variety is spectacular because of its upright arching tree shape, its prolonged broad and neat bracts, and its prolonged and large fruit of distinctive and attractive colors.

I claim:

1. A new and distinct variety of dogwood tree of the Japanese dogwood type, substantially as herein shown and described, characterized particularly as to novelty by the unique combination of a sturdy, graceful, upright arching, vase-shaped habit of growth, smooth exfoliating bark, attractive yellowish-green leaves which turn bright deep red in autumn and are retained on the tree as one of the last of the deciduous trees to drop its leaves, large showy, neat flowers, which are composed of broadly based overlapping bracts which curve to pointed tips and remain slightly cupped and present a crisp sculptured appearance throughout the flowering season which begins early in the month of June and extends well into July in Massachusetts, a distinctive and attractive flower color which is a creamy white color when the flowers first appear and then turning pure white in a few days, but sometimes having a pale pink tinge when opening and again when ready to drop, large attractive and longlasting fruit which gradually turn in color from yellow-green, to yellow, to orange and then to bright red until the fruit drops, with some fruit in these various color stages being on the tree at the same time throughout most of the season, excellent hardiness to at least —20° F. without injury, and especial suitability for planting in patios, lawns, alleys, and to flank features of special interest.

No references cited.

ROBERT E. BAGWILL, Primary Examiner